United States Patent [19]

Goss et al.

[11] 4,233,840

[45] Nov. 18, 1980

[54] METHOD FOR EVALUATION OF THE RESPONSE OF DIFFERENT CORES TO A RECOVERY PROCESS AND APPARATUS THEREFOR

[75] Inventors: Michael J. Goss, Cochrane; David A. Redford, Fort Saskatchewan, both of Canada

[73] Assignee: Texaco Canada Inc., Calgary, Canada

[21] Appl. No.: 34,233

[22] Filed: Apr. 30, 1979

[51] Int. Cl.³ .............................................. E21B 49/00
[52] U.S. Cl. .................................................... 73/153
[58] Field of Search ............ 73/153, 15.6, 825, 432.50

[56] References Cited

U.S. PATENT DOCUMENTS

| | | | |
|---|---|---|---|
| 2,786,977 | 3/1957 | Blagg et al. | 73/153 X |
| 3,018,660 | 1/1962 | Schmid | 73/153 |

*Primary Examiner*—Jerry W. Myracle
*Attorney, Agent, or Firm*—Carl G. Ries; Robert A. Kulason; Robert B. Burns

[57] ABSTRACT

Method and apparatus for subjecting discrete core specimens which have been removed from a subterranean strata or formation, and which contain an amount of bitumen, to a test procedure whereby to evaluate the response of different subterranean formations to a specified recovery process.

13 Claims, 2 Drawing Figures

4,233,840

METHOD FOR EVALUATION OF THE RESPONSE OF DIFFERENT CORES TO A RECOVERY PROCESS AND APPARATUS THEREFOR

BACKGROUND OF THE INVENTION

The production or recovery of crude oil or bitumen from viscous substances depends from the point of view of efficiency on the praticular method used. In the instance of withdrawal of crude oil from a reservoir, the producing technique is relatively inexpensive in contrast to the producing of bitumen from a substrate comprising tar sand and similar bitumen-bearing substances. On a trial basis the producing of tar sands to achieve any desirable output of bitumen, far exceeds the cost of producing crude oil.

However, because of the known limited crude oil sources and reservoirs it has become necessary to use diligence toward developing every known method for producing tar sand sources. Basically it is known that a certain quantity of bitumen can be obtained through various processes depending on the character of the substrate or the source from which the bitumen is obtained.

Among the most prevalent means for achieving such production is through stimulation. In this process steam is among the most extensively used recovery media. In different procedures, steam has even been successful in producing oil at commercial rates where pay is thick, viscosities at reservoir conditions are low, and some reservoir energy exists.

By way of example, in one embodiment of a steam stimulation process, high pressure steam containing natural gas, is forced into an unconsolidated substrate at a pressure sufficient to part or break up the deposit. In effect, the injected steam heats and fractures the deposit; it thereby creates an irregular heated area around the injection well. Following said injection heating period, which normally lasts up to several weeks, the well is put on production. Heated bitumen then moves through the substrate and into the producing well.

In another embodiment of the producing technique, the oil sands are underlain by a highly permeable zone. It has been proposed in such instance that steam be injected into this zone. Following the achievement of communication, pressure within the zone is built up and depleted in a number of cycles. This sequence causes the overlying bitumen to be heated and driven to the production well by a combination of gravity drainage and pressure depletion gradients.

It is clear then, that because of the varied composition of the substrate and tar sands within which the bitumen is contained, a particular injection process is preferably tailored to meet specific substrate conditions. Among the most pertinent variable characteristics, viscosity of the flowable material is primary. Viscosity measurements are available for example for the temperature range of from 60° to 250° F. Some extrapolation can be made into lower and higher ranges. However, no data is available to suggest viscosity in the temperature ranges up to 700° F. which are important for in-situ recovery operations.

Another factor to be considered in assessing a substrate is its permeability. A fundamental parameter such as permeability of the substrate, must be known as a function of bitumen concentration as well as of grain size distribution. Also desirable is a knowledge of how the various minerals are arranged in the formation. For example, if bitumen occupies 100% of the void space then at reservoir conditions the formation is impermeable. If, however, water occupies 100% of the void space then obviously many oil and tar sands are highly permeable.

In many recovery techniques and operations, a complex set of chemical reactions takes place. For example, it is known that air reacts with bitumen at room temperature, and in varying degrees of temperature right up to the combustion temperature of carbon. Such knowledge aids in evaluating air requirements for combustion operations. It further indicates the desirability of controlling the oxidation temperature. Even without the presence of oxygen, bitumen undergoes a complex set of thermal changes which eventually lead to the deposition of coke.

It is known further that many hydrocarbons precipitate asphaltenes from bitumen. However, little knowledge is available on the critical pressure, temperature, or concentration ranges in which asphaltenes are fully or partially precipitated. The degree, nature, and extent of such precipitation is essential information in planning any in-situ recovery operation.

The interaction within a substrate of injected materials with the mineral matrix at the temperatures and pressures used in many recovery operations, can result in severe changes to the matrix. This will result in the solution and reprecipitation of mineral components and/or changes of some minerals into others. Examples of this are the solution and reprecipitation of quartz, or the accelerated formation of montmorillonite. Such effects can adversely affect flow patterns, and therefore require further study.

To more completely bring together the above reiterated elements and variables, it is desirable to determine the characteristics of a subterranean area to be produced. This is done most readily by the taking of samples. These normally take the form of core samples, which are extracted directly from the substrate through the use of special core-taking equipment.

Toward expediting the producing operation, it is further desirable to perform as many tests as possible. This is particularly important prior to the commencement of large scale operations in a particular field. Normally it is achieved by bringing a segment of the formation, such as for example a core or a number of cores, a mineral block, or reconstituted oil sands, into a controlled environment. In the latter, the sample unit is subjected to a similar set of conditions as are found in the actual field. Under the simulated conditions, in-situ recovery concepts can be tested in a rapid and less costly manner.

It is therefore a primary object of the invention to provide a method and the apparatus therefore which will permit core samples of a tar sand and similar bitumen-bearing substrate to be evaluated. Such evaluation will thus provide data and information necessary to determine which of the areas from which the cores were taken best respond to a specified recovery process and thus determine the location to produce on a large scale whereby to obtain the most efficient yield of bitumen from the field.

In brief, the disclosed method for evaluating individual subterranean samples or specimens, comprises a sequence of controlled steps. Primarily, core samples withdrawn from a particular field or area are subjected to one or more steps as required, to simulate a predetermined bitumen extraction process. The primary step is the heating of the core specimen by injection and withdrawal of the fluids from one end of said core. This is achieved through use of a medium such as steam which is injected in the desired amount, and for a particular time period, into the core specimen. As the bitumen component contained within the specimen is elevated in temperature, it separates therefrom either by gravity drainage or induced pressure gradients. Such pressure gradients may be induced by agents used and/or periodically reducing the injection pressure and/or alternating injection periods with production periods.

Thereafter by comparing the temperature and pressure response at the top of the core, the volume of bitumen obtained, and by further evaluating the character of the residual sand in the residual core sample, it is possible to determine the character of the response of different areas as an aid to field site selection.

DESCRIPTION OF THE DRAWINGS

FIGS. 1 and 2 illustrate a preferred embodiment of the present apparatus 10 for enclosing and testing core samples which includes in essence means forming a fluid-tight chamber 11. Holder 12 is provided with a specimen 13 which normally comprises a preformed, compact core which has been withdrawn from a section of the substrate to be produced and which presumably will comprise an exemplary amount of bitumen.

Figure 1:
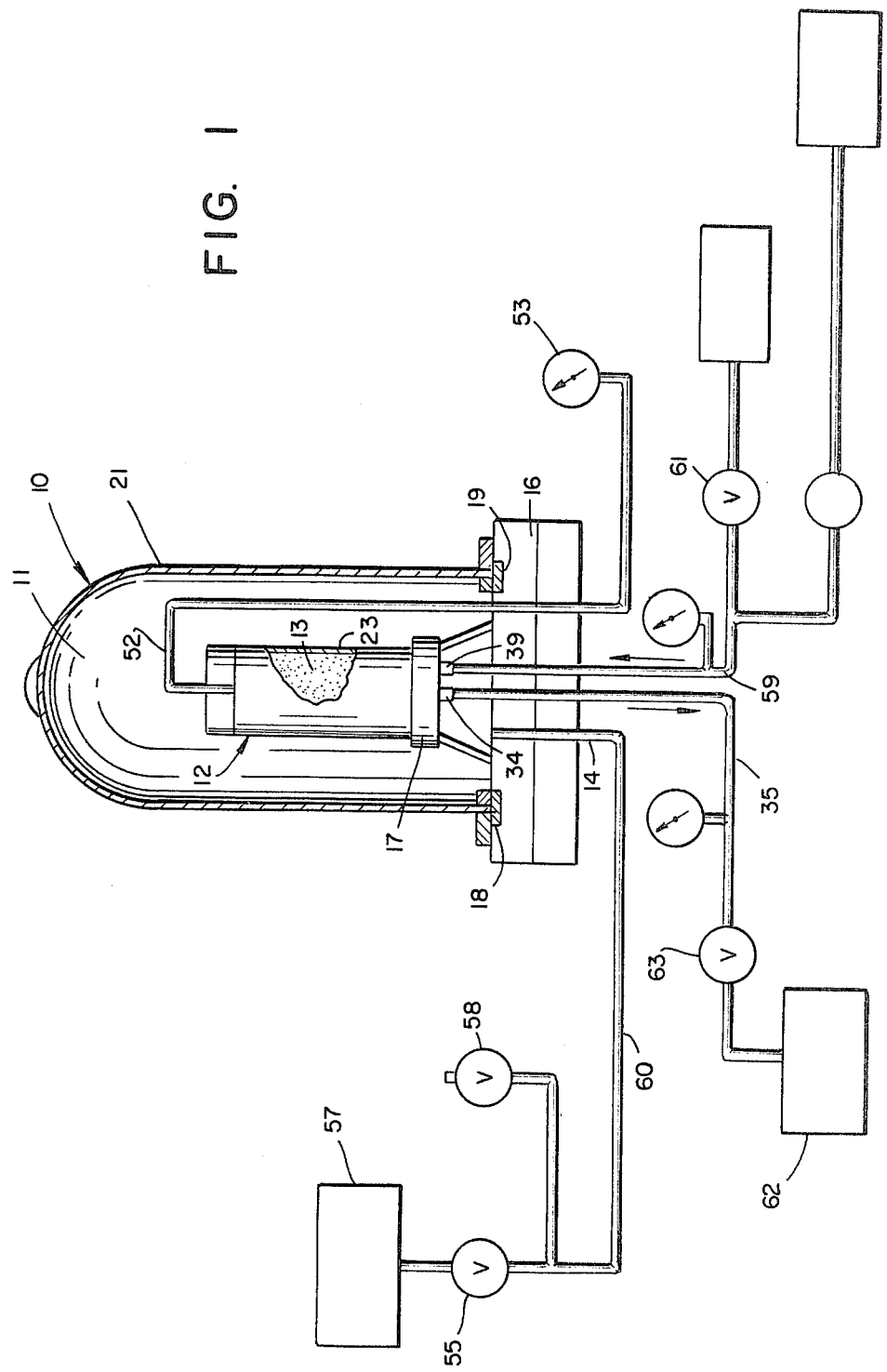
FIG. 1 is a schematic representation of the equipment used in the instant process.
Figure 2:
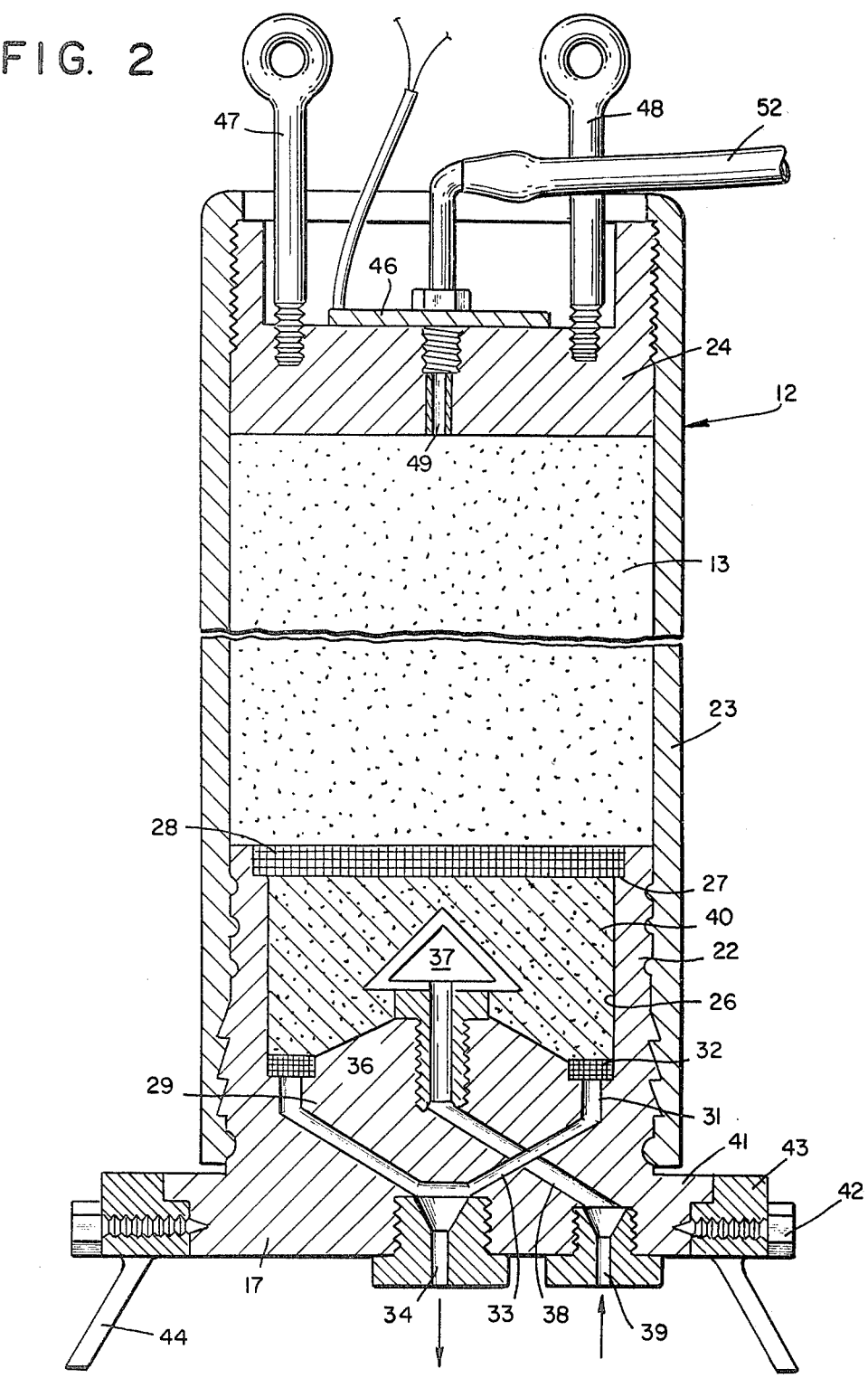
FIG. 2 is an enlarged view in cross section, taken along line 2—2 in FIG. 1.

Fluid-tight chamber 11 is so constructed that it can be readily opened and is further provided with an external connection 14. The latter communicates with means for accurately controlling the pressure therein whereby to perform necessary testing steps.

Physically, fluid-tight chamber 11 is formed by a base member 16 having a peripheral rim 18 at the upper edge, which is adapted to receive a gasket 19 or similar means for sealably engaging a housing 21. The latter is defined by an elongated member preferably of tubular form, having a peripheral lower lip which engages said gasket 19 to form a fluid-tight fit between the base member and housing when the two members are brought into contact. The upper end of housing 21 as shown is of generally circular cross section with a domed top.

Base member 17 of specimen holder 12, comprises primarily an upstanding body 22 onto which an elongated cylindrical specimen sleeve 23 is attached. The latter extends upwardly from body 22, being normally held in a vertical disposition for the testing purposes. Specimen sleeve 23 is primarily formed of a material sufficient to closely retain preformed core or specimen 13. Further, it can be formed with relatively thin walls of metal such as lead or a plastic type material such as viton.

It has been found that lead is a preferred embodiment of material when provided with a thin wall of approximately 1/32 inch. Such a wall thickness will permit transmission of hydrostatic pressure to the internal contained core sample. The upper end of specimen sleeve 23 is provided with a cover 24 of sufficient size to bear against the upper end of core sample 13 when the latter is in place.

Body 22 of base 17 is formed with an internal cylindrical cavity 26 which terminates at an upper peripheral lip or edge 27. Said peripheral lip 27 defines a means for supporting a screen 28, a filter, or similar permeable member. Said member 28 includes openings or interstices formed therein of sufficient size to freely pass a heating fluid upwardly into core sample 13.

The lower end of cavity 26 includes a floor 29 which is conformed generally to permit bitumen which has flowed from sample 13, to pass downwardly into a collector groove 31. Thus, cavity 26 is provided with a sand pack 40 or similar pervious mass which substantially fills the cavity.

The contoured surface of floor 29 is generally conical in shape, having the collector groove 31 formed at the lower edge thereof. Thus, bitumen which has become liquefied due to heating of core 13, flows from the core and will pass downwardly and onto the sloping floor 29. Groove 31 can be provided as shown with a circular screen 32 which, upon passing the bitumen therethrough, will filter the latter prior to its entering passages 33. The latter will accumulate bitumen and direct it into a discharge or drain port 34.

Heating fluid is introduced to core sample 13 by way of a nozzle 36. The latter as shown, is removably threaded into a threaded socket in the floor 29. Nozzle 36 includes means to receive a stream of heating fluids such as steam, which strikes deflector 37 and is directed radially outward. The steam is then dispersed throughout sand pack 40 in a relatively uniform flow. Conduit means 38 formed in the body 22 is communicated with the lower end of nozzle 36 and terminates at the fluid inlet port 39.

The lower end of body 22 is provided with a flange 41 together with a support ring 43. The latter is held in place against the flange by a plurality of fastening means such as radially positioned screws 42. Ring 43 includes a sufficient number of downwardly extending support legs 44 to support the specimen holder within fluid-tight chamber 11. Cover 24, engaged with sleeve 23, forms a closure plate to the sample holder 12 and firmly positions the sample in place. Said cover 24 includes means to receive lifting members 47 and 48. A thermocouple and heat flux transducer 46 is disposed at the upper surface of cover 24 and a pressure tap 49 opens onto the sample upper end. Said tap 49 is communicated by way of conduit 52 with a pressure transducer 53.

OPERATING PROCEDURE

In the practice of the invention, normally a particular subterranean area or working site is evaluated by obtaining a number of samples from that area. The sampling phase comprises the gathering of cores by a drilling process. In such a process, by the use of well known core collecting tools, the requisite core samples can be taken at various locations and at various depths. The number taken and their spacing will be such as to best obtain a composite of the character of the substrate.

As each core sample is withdrawn from the substrate, it is immediately frozen to maintain its shape prior to being tested. Thereafter, each core sample is subjected to the testing procedure such that in view of the results obtained, the respective subterranean areas can be compared as to their response to a given simulated recovery process.

Referring to the figures, the sample holder is prepared by first placing sleeve 23 onto base 17 and then inserting a core or sample 13 into sleeve 23. Cover 24 is inserted into the sleeve upper end and onto the top of the sample.

With the sample holder 12 in place on base 17, housing 21 is sealably connected to the base 16 thereby forming a closed atmosphere in chamber 11 about the sample.

To establish a desired environment within the fluid-tight chamber 11, to simulate the overburden pressure at the location from which the core sample 13 is withdrawn, said chamber is pressurized. The pressurizing medium in the present instance comprises the introduction at a predetermined pressure, of an inert gas such as nitrogen. Upon occupying chamber 11, said gas will exert a uniform pressure against sleeve 23 equivalent to the predetermined pressure in the substrate from which the core 13 was withdrawn. Pressure within said chamber 11 is regulated through control valve 55 which in turn is connected to a source of pressurizing medium 57 by a line 60, as well as to a vent means 58 for discharging the gas at a desired time.

Gas pressure acting on core 13 can be as much as desired within the pressure rating limit of the equipment and which as noted, is transmitted uniformly to all sides of the core holder sleeve 23.

To properly simulate the stimulation and producing steps, a flow of heating medium is introduced to the apparatus to contact the compressed core specimen 13. As shown in FIG. 1, the heating medium, in the preseent instance steam, is introduced by way of a steam line 59. The latter passes through base 16, being regulated by control valve 61 whereby to approximate the condition to which the substrate, represented by sample 13, will eventually be subjected. Steam enters directly into specimen holder 12 by way of passage 39, conduit 38, and nozzle 36. In the latter, the steam stream is dispersed outwardly by deflector 37 to be disseminated throughout the gravel or sand pack 40.

Steam, upon disseminating throughout pack 40, will continue to rise and after passing through screen 28, will continue to flow into sample 13. The temperature and pressure at the top of the core are measured continuously by thermocouple 46 and pressure transducer 53. With continued steam injection, the temperature of sample 13 will rise. Responsive to the temperature rise, physical properties of bitumen within sample 13 will be reduced and the bitumen will flow downwardly toward screen 28 and/or be forced down by pressure gradients. Such pressure gradients may be induced by agents used and/or periodically reducing the injection pressure and/or alternating injection periods with production periods.

The steam injection stimulation is continued for a predetermined period to foster bitumen flow. The liquid, after flowing through the sand pack 40, will enter collecting groove 31. Thereafter the liquid bitumen is directed through passage 33 to discharge opening 34 from which it is further directed by line 35 to a liquid production facility 62 by way of valve 63. Thereafter, the condition in the chamber 11 is stabilized by venting the interior thereof through valve 58 to the atmosphere such that the upper housing 21 can be removed.

The core 13 is removed from sleeve 23 and its bitumen content determined. Thereafter, as subsequent cores from different sites are similarly tested, analysis of the residual core material together with bitumen production history and temperature and pressure response at the top of the core will provide an indication of the responses of the various areas, represented by the cores.

Other modifications and variations of the invention as hereinbefore set forth can be made without departing from the spirit and scope thereof, and therefore, only such limitations should be imposed as are indicated in the appended claims.

We claim:

1. Apparatus for treating a core specimen (13) of substrate which contains an amount of bitumen therein, to separate at least a part of the contained bitumen from the core specimen, which apparatus includes;

enclosure means (16, 21) defining a disconnectable fluid-tight chamber (11) communicated with a source of pressurizing gas (57, 14) for controlling the atmosphere within said chamber (11), a specimen holder (12) removably positioned within said fluid-tight chamber (11) and having an enclosing sleeve (23) adapted to receive said core specimen (13), conduit means communicating said specimen holder (12) with a source of a heating fluid for injecting a stream of said heating fluid into the specimen holder, whereby to raise the temperatures of a pressurized specimen (13) and thereby lower the viscosity of bitumen contained in said specimen, at the lower end of said specimen holder (12) defining a collector (31) to receive bitumen which flows downwardly from said heated specimen (13).

2. In an apparatus as defined in claim 1, wherein said specimen holder includes; a member having a porous bed at the lower end thereof, and means for introducing heating fluid through said bed for heating said specimen.

3. In an apparatus as defined in claim 2, wherein said means for introducing a heating fluid into said specimen includes; a permeable filter disposed beneath the specimen to receive and disseminate a heating fluid.

4. In an apparatus as defined in claim 1, including; means for extracting fluidized bitumen from said fluid-tight chamber concurrently with the means of injecting heated fluid.

5. In an apparatus as defined in claim 1, including; means for injecting heated fluids into said fluid-tight chamber and for concurrently removing fluids from the same side of core specimen contained in said fluid-tight chamber.

6. Method for evaluating a prospective bitumen-containing subterranean strata for determining the amenability of said strata to a hot fluid stimulation injection for producing said bitumen, which method includes the steps of;

withdrawing at least one core sample from the substrate, subjecting said core sample to a confining pressure equivalent to the pressure at the substrate from which the sample was withdrawn, introducing a flow of heating fluid into the pressurized substrate sample for a predetermined period, said heating fluid being at a temperature sufficient to fluidize said sample, and being introduced for a period of time to cause fluidization of the sample whereby contained bitumen will be converted into a flowable condition, and collecting the fluidized bitumen which has flowed from said sample.

7. In the method as described in claim 6, including; the repetition of the respective steps upon samples from varied samples in said substrate.

8. In the method as described in claim 6, including; the steps of varying the amount and the condition of the hot fluid introduced to said sample whereby to determine the optimum amount of bitumen so produced.

9. In the method as described in claim 6, including; the step of determining the amount of bitumen remaining in said core sample subsequent to said hot fluid injection step.

10. In the method as described in claim 6, including; the step of continuing the period of hot fluid injection introduced into said core sample.

11. In the method as described in claim 6, including; the step of continuously measuring the temperature at upper end of said core sample.

12. In the method as described in claim 6, including; the step of continuously measuring the pressure at upper end of said core sample.

13. In the method as described in claim 6, including; the step of periodically reducing the injection pressure and/or alternating injection periods with production periods.

* * * * *